United States Patent
Nakahira et al.

(10) Patent No.: US 9,623,075 B2
(45) Date of Patent: Apr. 18, 2017

(54) TYPE A2 BOTULINUM TOXIN PREPARATION

(71) Applicants: Shinji Nakahira, Kumamoto (JP); Yasushi Torii, Kumamoto (JP); Yoshitaka Goto, Kumamoto (JP); Miho Shinmura, Kumamoto (JP); Satomi Munechika, Kumamoto (JP); Sachio Okuda, Kumamoto (JP); Shunji Kozaki, Sakai (JP)

(72) Inventors: Shinji Nakahira, Kumamoto (JP); Yasushi Torii, Kumamoto (JP); Yoshitaka Goto, Kumamoto (JP); Miho Shinmura, Kumamoto (JP); Satomi Munechika, Kumamoto (JP); Sachio Okuda, Kumamoto (JP); Shunji Kozaki, Sakai (JP)

(73) Assignee: THE CHEMO-SERO THERAPEUTIC RESEARCH INSTITUTE, Kumamoto-shi (JP)

( * ) Notice: Subject to any disclaimer, the term of this patent is extended or adjusted under 35 U.S.C. 154(b) by 388 days.

(21) Appl. No.: 13/903,731

(22) Filed: May 28, 2013

(65) Prior Publication Data
US 2013/0252902 A1 Sep. 26, 2013

Related U.S. Application Data

(62) Division of application No. 12/935,769, filed as application No. PCT/JP2009/056613 on Mar. 31, 2009, now abandoned.

(30) Foreign Application Priority Data

Mar. 31, 2008 (JP) ................................. 2008-092145

(51) Int. Cl.
*A61K 38/48* (2006.01)
*A61K 38/16* (2006.01)

(52) U.S. Cl.
CPC ........ *A61K 38/164* (2013.01); *A61K 38/4893* (2013.01)

(58) Field of Classification Search
None
See application file for complete search history.

(56) References Cited

U.S. PATENT DOCUMENTS

| | | | | |
|---|---|---|---|---|
| 7,964,199 B1* | 6/2011 | Bigalke et al. | | 424/247.1 |
| 8,540,987 B2* | 9/2013 | Azuma et al. | | 424/130.1 |
| 8,557,255 B2* | 10/2013 | Marx | | A61K 38/4893 424/239.1 |
| 8,949,033 B2* | 2/2015 | Harakawa | | 702/19 |
| 9,095,523 B2* | 8/2015 | Marx | | A61K 38/4893 |
| 9,243,057 B2* | 1/2016 | Marks | | C07K 16/1282 |
| 9,278,133 B2* | 3/2016 | Harakawa | | A61K 9/0019 |
| 2001/0012833 A1 | 8/2001 | Aoki et al. | | |
| 2002/0010138 A1 | 1/2002 | Aoki et al. | | |
| 2005/0163809 A1 | 7/2005 | Kaji et al. | | |
| 2006/0153877 A1 | 7/2006 | Kozaki et al. | | |
| 2008/0003241 A1* | 1/2008 | Marx | | A61K 38/4893 424/239.1 |
| 2010/0173841 A1* | 7/2010 | Harakawa et al. | | 514/12 |
| 2011/0014211 A1* | 1/2011 | Azuma et al. | | 424/167.1 |
| 2011/0033431 A1* | 2/2011 | Nakahira et al. | | 424/93.41 |
| 2011/0217287 A1 | 9/2011 | Bigalke et al. | | |
| 2013/0252902 A1* | 9/2013 | Nakahira et al. | | 514/18.3 |

FOREIGN PATENT DOCUMENTS

| | | |
|---|---|---|
| DE | 199 25 739 A1 | 12/2000 |
| EP | 1 491 205 A1 | 12/2004 |
| EP | 1 508 336 A1 | 2/2005 |
| EP | 1 640 017 A1 | 3/2006 |
| JP | 11-507072 | 6/1999 |
| JP | 2003/505343 | 2/2003 |
| WO | WO 94/28922 | 12/1994 |
| WO | WO 96/11699 | 4/1996 |
| WO | WO 97/35604 A1 | 10/1997 |
| WO | WO 2008/050866 A1 | 5/2008 |

OTHER PUBLICATIONS

Akaike et al, J Physiol 591.4 (2013) pp. 1031-1043.*
Torii et al, Toxicon 77 (2014) 114-120.*
Dineen et al, FEMS Microbiology Letters, 2004, 235:9-16.*
Tabita et al, FEMS Microbiology Letters, 1991, 79:251-256.*
DasGupta et al, Biochimica et Biophysica Acta, 1970, 214:343-349.*
Volland et al, J. Immunological Methods, 2008, 330:120-129.*
Campbell et al, Biochimica et Biophysica Acta, 1993, 1216:487-491.*
Office Action issued Aug. 13, 2013 in Japanese Patent Application No. 2010-505929.
Extended European Search Report issued Mar. 8, 2013 in Patent Application No. 09726893.2.
Extended European Search Report issued Dec. 15, 2011, in Patent Application No. 09726893.2.
T. J. Smith, et al., "Sequence Variation within Botulinum Neurotoxin Serotypes Impacts Antibody Binding and Neutralization", Infection and Immunity, American Society for Microbiology, vol. 73, No. 9, XP 002392366, Sep. 2005, pp. 5450-5457.
A. Willems, et al., "Sequence of the gene coding for the neurotoxin of *Clostridium botulinum* type A associated with infant botulism: comparison with other clostridial neurotoxins", Research in Microbiology, vol. 144, No. 7, XP 023924679, Jan. 1993, pp. 547-556.

(Continued)

*Primary Examiner* — Nita M Minnifield
(74) *Attorney, Agent, or Firm* — Oblon, McClelland, Maier & Neustadt, L.L.P.

(57) ABSTRACT

A method for treating a patient who has a neutralizing antibody to a type A1 botulinum toxin. The method includes administering 150 kDa type A neurotoxin from type A2 *Clostridium botulinum* (A2 NTX) to the patient. In accordance with the present invention, a problem can be solved of decrease in clinical response caused by a neutralizing antibody to a type A1 botulinum toxin produced when a patient is treated with a pharmaceutical preparation containing a type A1 botulinum toxin.

20 Claims, 3 Drawing Sheets

(56) References Cited

OTHER PUBLICATIONS

Arnold William Klein, "Contradictions and Complications With the Use of Botulinum Toxin", Clinics in Dermatology, vol. 22, No. 1, XP 55012455, Jan. 2004, pp. 66-75.
M. F. Brin, et al., "Safety and efficacy of NeuroBloc (botulinum toxin type B) in type A-resistant cervical dystonia", Neurology, vol. 53, XP 55012448, Oct. 22, 1999, pp. 1431-1438.
Yasushi Torii, et al., "Efficacy of botulinum neurotoxin subtype A2 in rats producing neutralizing antibody against botulinum neurotoxin subtype A1", Toxicon, vol. 51, XP 022695752, Jun. 2008, pp. 21-22.
Yasushi Torii, et al., "Comparison of effects of botulinum toxin subtype A1 and A2 using twitch tension assay and rat grip strength test", Toxicon, vol. 57, No. 1, XP 027578664, Jan. 2011, pp. 93-99.
Joseph Jankovic, MD, "Botulinum toxin in movement disorders", Current Opinion in Neurology, vol. 7, 1994, pp. 358-366.
Ryuji Kaji, et al., "Dystonia and botulinum therapy", Shindan-To Chiryosha, 2005, pp. 52-97 (with partial English translation).
Genji Sakaguchi, et al., "Distinct characters of Clostridium botulinum type A strains and their toxin associated with infant botulism in Japan", International Journal of Food Microbiology, vol. 7, 1990, pp. 231-241.
Toru Kubota, et al., "Gene arrangement in the upstream region of Clostridium botulinum type E and Clostridium butyricum BL6340 progenitor toxin genes is different from that of other types", FEMS Microbiology Letters, vol. 158, 1998, pp. 215-221.
Toru Kubota, et al., "Mosaic Type of the Nontoxic-Nonhemagglutinin Component Gene in Clostridium botulinum Type A Strain Isolated from Infant Botulism in Japan", Biochemical and Biophysical Research Communications, vol. 224, Article No. 1110, 1996, pp. 843-848.
Shunji Kozaki, et al., "Immunological Characterization of the Neurotoxin Produced by Clostridium botulinum Type A Associated with Infant Botulism in Japan", Microbiol. Immunol., vol. 39, No. 10, 1995, pp. 767-774.
Juan J. Cordoba, et al., "Studies on the Genes Encoding Botulinum Neurotoxin Type A of Clostridium botulinum from a Variety of Sources", System. Appl. Microbiol., vol. 18, 1995, pp. 13-22.
Ryuji Kaji, et al., "Dystonia and botulinum therapy", Shindan-To Chiryosha, 1996, 17 pages (with partial English translation).
Dirk Dressler, et al., "Pharmacology of therapeutic botulinum toxin preparations", Disability and Rehabilitation, vol. 29, No. 23, Dec. 2007, pp. 1761-1768.
Mitchell F. Brin, MD, "Botulinum Toxin: Chemistry, Pharmacology, Toxicity, and Immunology", Muscle & Nerve Supplement 6, 1997, pp. S146-S168.
Hideyuki Arimitsu, et al., "Purification of Fully Activated Clostridium botulinum Serotype B Toxin for Treatment of Patients with Dystonia", Infection and Immunity, vol. 71, No. 3, Mar. 2003, pp. 1599-1603.
Chun K. Tse, et al., "Preparation and Characterisation of Homogeneous Neurotoxin Type A from Clostridium botulinum", Eur. J. Biochem., vol. 12, 1982, pp. 493-500.
Shunji Ozaki, et al., "On Similarity and Difference between Toxins Produced by Type A *Clostridium botulinum* derived from Infant Botulism and Produced by Ordinary Type A Clostridium botulinum", Nippon Jui Gakkai Gakujutsu Shukai Koen Yoshishu, vol. 113, 1992, p. 216 (with English translation).
Shoji Nakagami, et al., "On Property of Toxin Produced by Type A *Clostridium botulinum* derived from Infant Botulism", Nippon Jui Gakkai Gakujutsu Shukai Koen Yoshishu, vol. 111, 1991, p. 230 (with English translation).
Kathryn Campbell, et al., "Nucleotide sequence of the gene coding for Clostridium botulinum (*Clostridium argentinense*) type G neurotoxin: genealogical comparison with other clostridial neurotoxins", Biochimica et Biophysica Acta, vol. 1216, 1993, pp. 487-491.
Hervé Volland, et al., "A sensitive sandwich enzyme immunoassay for free or complexed Clostridium botulinum neurotoxin type A", Journal of Immunological Methods, vol. 330, 2008, pp. 120-129.
Dineen et al (2004), FEMS Microbiology Letters, 235, pp. 9-16.

\* cited by examiner

Fig. 1

| | Structure | Molecular Weight (kDa) |
|---|---|---|
| LL Toxin | NTX NTNH HA / NTX NTNH HA | 900 |
| L Toxin | NTX NTNH HA | 500 |
| M Toxin | NTX NTNH | 300 |
| S Toxin | NTX | 150 |

A1 NTX

TYPE A2 BOTULINUM TOXIN PREPARATION

CROSS-REFERENCE TO RELATED APPLICATIONS

This application is a Divisional of U.S. patent application Ser. No. 12/935,769 filed Sep. 30, 2010, which is a National Stage of PCT/JP09/056,613 filed Mar. 31, 2009, and claims priority to Japanese Patent Application No. 2008-092145 filed Mar. 31, 2008, the entire contents of which are hereby incorporated by reference.

TECHNICAL FIELD

The present invention, for addressing decrease in clinical response due to a neutralizing antibody to a botulinum toxin from type A1 *Clostridium botulinum* (type A1 botulinum toxin), as occasioned when a patient is treated with a pharmaceutical preparation containing type A1 botulinum toxin, relates to a pharmaceutical preparation for administering to a patient suffering from a disease with a muscle overactivity an effective dosage amount of a type A neurotoxin (A2 NTX) of 150 kDa obtained from hemagglutinin (HA)-negative, type A2 *Clostridium botulinum* isolated as infant botulism pathogen, and a method for treating a patient having a neutralizing antibody to a type A1 botulinum toxin using said pharmaceutical preparation.

BACKGROUND ART

A botulinum toxin produced by *Clostridium botulinum*, anaerobic Gram-positive bacteria, is the most lethal neurotoxin on earth. It is classified into seven types, A, B, C, D, E, F and G, and the property of each type has been elucidated. The types are distinguishable from each other by respective type-specific neutralizing antibodies. Depending on the types, a botulinum toxin may vary in animal species it may affect, severity of paralysis it induces, duration of time of its action, and the like. An active center protein of a botulinum toxin has a molecular weight of about 150 kDa (NTX) as common in all the known seven types.

Any botulinum toxin, when produced from *Clostridium botulinum*, is in a molecular form of a complex composed of NTX and relevant nontoxic proteins. A type A botulinum toxin is produced in a molecular form of either 900 kDa (LL toxin), 500 kDa (L toxin), or 300 kDa (M toxin) (FIG. 1). These LL, L and M toxins are called a botulinum toxin complex or a progenitor toxin. The botulinum toxins are separate to release NTX and NTNH (a nontoxic non-HA protein) under alkaline conditions (pH 7.2 or higher). By utilizing this property, it is possible to isolate NTX of 150 kDa (an active center protein that endows a neurotoxin with the activity; also called "S toxin") alone.

The botulinum toxins are, upon absorption in the upper small intestine, separate to release nontoxic proteins and a neurotoxin in a lymphatic vessel. The released neurotoxin is then bound to a receptor at the nerve end at its C-terminus of a heavy chain and taken into neurons via the receptor. Then, it specifically cleaves a protein in the presynaptic membrane through a light chain zinc methaloendopeptidase activity and inhibits a calcium-dependant release of acetylcholine to thereby block neuromuscular transmission at the synapse (Non-patent reference 1).

Although a botulinum toxin is a neurotoxin that may lead human to death in botulinum intoxication through blockage of systemic neuromuscular transmission, it may also be utilized as a remedy for treating a disease with a muscle overactivity such as e.g. dystonia by positively making use of its activity and by administering directly into the muscle of a patient suffering from the disease so that a local muscular tension may be relieved (Non-patent reference 2). For instance, a type A botulinum toxin complex (Allergan Inc., BOTOX®; has been approved as a medicament for treating blepharospasm, strabismus, hemifacial spasm, and cervical dystonia, and for treating wrinkles at the middle of the forehead by the Food and Drug Administration (FDA). A type B botulinum toxin complex (Elan Pharmaceuticals, MYOBLOC®; has also been approved as a medicament for treating cervical dystonia by FDA. It is said that a type A botulinum toxin has a higher potency and a longer duration of action as compared to types other than a type A botulinum toxin. An average duration of action of a type A botulinum toxin from its single intramuscular administration up till amelioration of symptoms is typically about 3 to 4 months.

Therapeutic preparations of botulinum toxin are available from Allergan Inc. (U.S.A.), Ipsen Limited (U.K.) or Elan Pharmaceuticals (Ireland). These commercially available therapeutic preparations of botulinum toxin consist of a purified botulinum toxin complex (LL toxin) alone in a molecular structure with bound relevant nontoxic proteins. For instance, the currently commercially available therapeutic preparations of type A botulinum toxin, i.e. BOTOX® from Allergan Inc. and Dysport® from Ipsen Limited, consist of an LL toxin of a botulinum toxin complex comprising as its component an HA protein such as HA17, HA34, or HA70.

In recent years, type A NTX preparations (Merz Pharma, Xeomin®, Germany) comprising no nontoxic proteins were sold in 2005, similar other preparations underwent clinical trials in the U.S.A. and development of next-generation preparations has actively been done.

On the other hand, a botulinum toxin isolated from patients suffering from infant botulism in 1990, though belonging to type A, consists of M toxin with no HA proteins (HA-negative). Type A *Clostridium botulinum* that produces M toxin with no HA protein has been first identified in Japan in 1986 from patients suffering from infant botulism (Non-patent reference 3). The clinically isolated strains include Kyoto-F, Chiba-H, Y-8036, 7I03-H, 7I05-H and KZ1828. When compared with the other types A to G of botulinum toxins, a botulinum toxin from *Clostridium botulinum* that causes infant botulism is a peculiar neurotoxin distinct from any types of these toxin molecules.

From the genetic point of view, a genetic mechanism of *Clostridium botulinum* as infant botulism pathogen is different from those of the other types of botulinum toxin. Most of the conventional botulinum toxins, typically type A botulinum toxin, has been seen as a botulinum toxin complex having Haemagglutinin (HA) protein as a component thereof. Genes coding for HA proteins such as HA17, HA34 and HA70 are contained in neurotoxin genes of types A, B, C, D and G *Clostridium botulinum* but are completely absent in those of *Clostridium botulinum* as infant botulism pathogen. Also, genes of *Clostridium botulinum* as infant botulism pathogen contain a regulator gene such as p47 (Non-patent reference 4). Besides, it was shown that a sequence of the NTNH protein of botulinum toxin produced by *Clostridium botulinum* as infant botulism pathogen is a miscellany, i.e. a mosaic, of nontoxic non-HA protein NTNH genes of type C and type A (Non-patent reference 5 and Non-patent reference 6).

As for NTX molecules per se, a molecular weight is distinct from each other in that a heavy chain of the conventional type A botulinum toxin is 93 kDa whereas botulinum toxin produced by *Clostridium botulinum* as infant botulism pathogen is 101 kDa. They also show different protease reactivity (Non-patent reference 7). The amino acid sequences of these two isotypes of the botulinum toxins are different by 10.1% as a whole and, by 13% in the heavy chain region and by as low as 4.9% in the light chain region (Non-patent reference 8).

It is reported that cell strains used for manufacturing commercially available preparations of type A botulinum toxin are HALL strain for BOTOX® and Xeomin® and NCTC2916 strain for Dysport® (Non-patent reference 9 and Non-patent reference 10), which may be classified into type A botulinum toxin which comprises HA protein, i.e. type A1 botulinum toxin. On the other hand, botulinum toxin produced by *Clostridium botulinum* as infant botulism pathogen may be classified into type A2 botulinum toxin.

In recent years, a problem has been presented that repetitive administration of botulinum toxin may induce production of an anti-botulinum toxin antibody to diminish efficacy of the botulinum toxin. For instance, it is reported that an antibody induction in BOTOX® is 3 to 10% (Non-patent reference 11). It is pointed out that, as one of the causes, HA contained in therapeutic preparations has an adjuvant activity for antibody production (Non-patent reference 12), which adjuvant activity is thought to facilitate production of a neutralizing antibody to NTX.

For a highly purified botulinum toxin, it was formerly reported by Tse C K., et al. (Non-patent reference 13) and also in WO1996/11699 (Patent reference 1) as to a process for purification (p. 6, line 9 to p. 7, line 2) and pharmaceutical compositions (p. 11, Table 2).

Patent reference 1: WO1996/11699
Non-patent reference 1: Jankovic J. et al., Curr. Opin. Neurol., (7): p. 358-366, 1994
Non-patent reference 2: Ryuji Kaji et al., "Dystonia and botulinum therapy", Shindan-To-Chiryosha, 2005
Non-patent reference 3: Sakaguchi G. et al., Int. J. Food Microbiol., 11: p. 231-242, 1990
Non-patent reference 4: Kubota T. et al., FEMS Microbiology letters., 158: p. 215-221, 1998
Non-patent reference 5: Kubota T. et al., Biochem. Biophys. Res. Commun., 224(3): p. 843-848, 1996
Non-patent reference 6: Sakaguchi G. et al., Int. J. Food Microbiol. 11: p. 231-242, 1990
Non-patent reference 7: Kozaki S. et al., Microbiol. Immunol. 39(10): p. 767-774, 1995
Non-patent reference 8: Cordoba J. et al., System. Appl. Microbiol. 18: p. 13-22, 1995
Non-patent reference 9: Ryuji Kaji et al., "Dystonia and botulinum therapy", Shindan-To-Chiryosha: 23, 1996
Non-patent reference 10: Dressler D. et al., Disabil Rehabil. 29(23): p. 1761-1768, 2007
Non-patent reference 11: Brin M F., Muscle Nerve Suppl., 6: p. 146-168, 1997
Non-patent reference 12: Arimitsu H. et al., Infect. Immun., 71(3): p. 1599-1603, 2003
Non-patent reference 13: Tse C K. et al., Eur. J. Biochem., 122(3): p. 493-500, 1982

DISCLOSURE OF THE INVENTION

Technical Problem to be Solved by the Invention

Botulinum toxin is known efficacious for the treatment of patients suffering from a disease with a muscle overactivity through relaxation of the muscles. However, a problem has been presented that repetitive administration of botulinum toxin may diminish its efficacy in patients. This phenomenon is thought to be due to production of antibodies against the toxin. It is pointed out that, as one of the causes, Haemagglutinin (HA) contained in therapeutic preparations has an adjuvant activity for antibody production. Therefore, it is necessary to address decrease in clinical response due to a neutralizing antibody produced by repetitive administration of botulinum toxin.

Means for Solving the Problems

Currently commercially available therapeutic preparations of type A botulinum toxin consist of a purified LL toxin alone in a molecular structure with bound relevant nontoxic proteins. It is reported that cell strains used for manufacturing commercially available preparations of type A botulinum toxin are HALL strain for BOTOX® and NCTC2916 strain for Dysport® (Non-patent reference 9), which may be classified into type A botulinum toxin which comprises HA protein, i.e. type A1 botulinum toxin.

Prior to the present invention, the present inventors have focused, among type A botulinum toxins, on botulinum toxins produced by type A subspecies *Clostridium botulinum* distinct from the commercially available type A1 botulinum toxins. This is a type A botulinum toxin isolated from patients suffering from infant botulism in 1990 that comprises no HA proteins but M toxin and is classified into type A2 botulinum toxin. The amino acid sequences of these two isotypes of botulinum toxins, i.e. A1 and A2, are different by 10.1% as a whole and, by 13% in the heavy chain region and by as low as 4.9% in the light chain region. As such, since the amino acid sequences of these two isotypes of botulinum toxins are quite similar to each other, the idea of therapy to use type A2 botulinum toxin has not been conceived for solving the therapeutic problem that repetitive administration of the conventional type A1 botulinum toxin may diminish its efficacy in patients who developed a neutralizing antibody.

Furthermore, the present inventors have succeeded in highly purifying type A2 botulinum toxin, which is a type A botulinum toxin isolated from patients suffering from infant botulism in 1990 and is prepared by removing a nontoxic component from M toxin, which comprises no HA proteins, and highly purifying NTX.

The present inventors have constructed "Model Rat with decreased response to botulinum toxin", which has a neutralizing antibody to the hitherto known type A1 botulinum toxin and thus has decreased efficacy for the immunized toxin, by administering subcutaneously a plurality of the toxin to a rat for immunization. Furthermore, the present inventors have administered a highly purified type A2 botulinum toxin (A2 NTX) to this Model Rat to confirm its neuromuscular transmission blocking effect using a test system with an electromyograph, i.e. a rat CMAP test wherein a compound muscle action potential (CMAP) is measured at the gastrocnemius muscle of rats. Besides, the present inventors have reacted human serum containing an anti-type A1 botulinum toxin antibody with A2 NTX and confirmed neuromuscular transmission blocking effect of the reaction mixture using the rat CMAP test. The present inventors have thereby proved possibility of a novel therapeutic method with a highly purified type A2 botulinum toxin.

Thus, the present invention includes the inventions (1) to (6) as follows:

(1) A pharmaceutical preparation for use in a patient who has a neutralizing antibody to a botulinum toxin from type A1 *Clostridium botulinum* (type A1 botulinum toxin), said preparation comprising as an active ingredient 150 kDa type A neurotoxin from type A2 *Clostridium botulinum* (A2 NTX).
(2) A medicament for treating a disease with muscle overactivity for use in a patient who has a neutralizing antibody to a type A1 botulinum toxin, said medicament comprising as an active ingredient A2 NTX.
(3) A method for treating a patient who has a neutralizing antibody to a type A1 botulinum toxin, said method comprising administering A2 NTX to the patient.
(4) A method for treating a patient suffering from a disease with muscle overactivity who has a neutralizing antibody to a type A1 botulinum toxin, said method comprising administering A2 NTX to the patient.
(5) Use of A2 NTX in a patient who has a neutralizing antibody to a type A1 botulinum toxin.
(6) Use of A2 NTX in a patient suffering from a disease with muscle overactivity who has a neutralizing antibody to a type A1 botulinum toxin.

Effects of the Invention

The highly purified botulinum toxin (A2 NTX) according to the present invention from HA-negative *Clostridium botulinum* isolated from infant botulism pathogen has a therapeutic effect to a patient who has a neutralizing antibody to a type A1 botulinum toxin. Besides, as not comprising HA, A2 NTX is less likely to induce antibody production.

Furthermore, A2 NTX is useful for use as a pharmaceutical preparation for addressing decrease in clinical response caused by a neutralizing antibody to a type A1 botulinum toxin produced when a patient is treated with a pharmaceutical preparation comprising a type A1 botulinum toxin. Therefore, A2 NTX is useful for use as a medicament for treating a disease with muscle overactivity such as strabismus, blepharospasm, hemifacial spasm, spasmodic torticollis, post-stroke spasticity, cerebral palsy, spasmodic dysphonia, headache such as migraine, chronic pain such as lumbago, the stiffness in the shoulders, paresis occurring at the onset of Parkinson disease or multiple sclerosis, myofascial pain syndrome, spasm of the masticatory muscles, chronic anal fissure, overactive bladder, bruxism, facial myokymia, tic, local dystonia, or wrinkle.

BRIEF DESCRIPTION OF DRAWINGS

FIG. 1 illustrates a molecular structure of a botulinum toxin protein complex.
FIG. 3 is a graph showing the reaction of human serum containing an anti-type A1 botulinum toxin antibody with A1 NTX (FIG. 3A) or A2 NTX (FIG. 3B). The axis of abscissas depicts the patient serum Nos. reacted with A1 NTX and A2 NTX whereas the axis of ordinates a dose of reactive toxins (U).

BEST MODE FOR CARRYING OUT THE INVENTION

Figure 2:
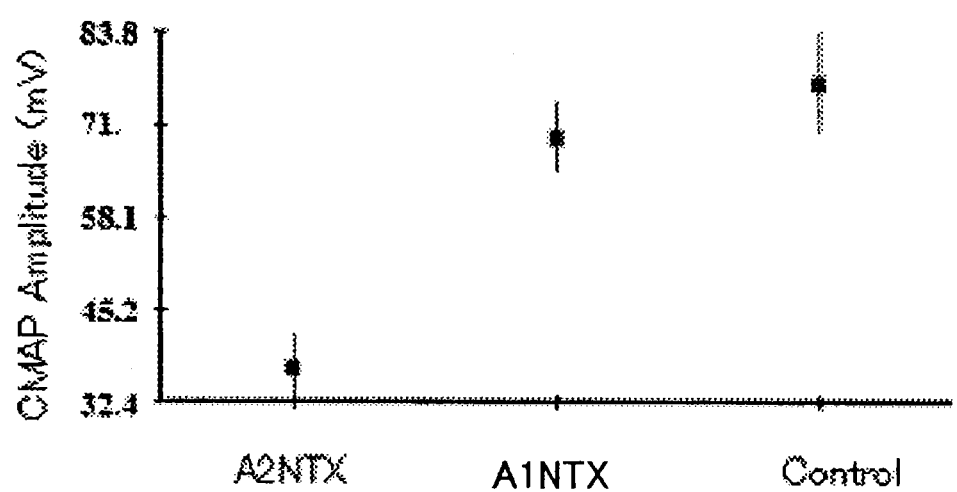
FIG. 2 is a graph showing the results of CMAP in the left hind leg muscle using Model Rat with decreased response to botulinum toxin. The axis of abscissas depicts the kind of toxins administered (NTX) whereas the axis of ordinates CMAP amplitude (mV).

The various aspects of the present invention are explained in detail hereinbelow.

The A2 NTX according to the present invention comprises as an active ingredient a highly purified type A botulinum toxin which is prepared by removing the nontoxic component from M toxin obtained from HA-negative type A2 *Clostridium botulinum* isolated from infant botulism pathogen, i.e. NTX. Since NTX may exert efficacy more rapidly after administration as compared to LL toxin or M toxin, the therapeutic medicament of the present invention may be used as one with more rapid efficacy. Also, A2 NTX is less diffusive and with a broader safety margin and thus may most suitably be used as a therapeutic medicament for decreasing local, muscle overactivity in a disease with a muscle overactivity. Besides, A2 NTX is useful for use as a pharmaceutical preparation for addressing decrease in clinical response caused by a neutralizing antibody to a type A1 botulinum toxin produced when a patient is treated with a pharmaceutical preparation comprising a type A1 botulinum toxin.

Such a type of botulinum toxin as isolated from patients suffering from infant botulism, though being type A, consists of M toxin without HA proteins. Type A *Clostridium botulinum* that produce botulinum toxin without HA proteins are selected from Kyoto-F, Chiba-H, Y-8036, 7I03-H, 7I05-H and KZ1828.

The therapeutic medicament of the present invention is preferably a pharmaceutical composition comprising the highly purified type A botulinum toxin from infant botulism pathogen and a stabilizing agent for botulinum toxin.

A stabilizing agent for botulinum toxin may stabilize a botulinum toxin under conditions under which the composition as described above is stored and would not impair rapid efficacy of treating efficacy to a disease with muscle overactivity. An example of a stabilizing agent for botulinum toxin includes a human serum albumin.

The preferable pharmaceutical composition of the present invention may be prepared by the step of mixing the highly purified type A botulinum toxin from infant botulism pathogen with a human serum albumin.

The highly purified type A botulinum toxin may be purified by a suitable combination of ion exchange chromatography, gel filtration chromatography, hydrophilic chromatography, and the like. Specifically, cells of *Clostridium botulinum* are removed from culture supernatant by filtration and the obtained M toxin is concentrated by e.g. the procedure using UF membrane. M toxin is then placed at pH 7 or more to be separated into a neurotoxin (NTX) and nontoxic proteins (NTNH). Then, the neurotoxin is crudely purified by e.g. cation exchange chromatography and the fractions with the toxic activity are collected and further purified by gel filtration chromatography. The toxic activity may be measured by e.g. intraperitoneal injection in mice, where the toxic activity is calculated from $LD_{50}$ after intraperitoneal administration in mice, and $LD_{50}$ in mice is defined as 1 unit.

After the purification step, any procedure may be taken insofar as comprising the step of mixing the botulinum toxin with a human serum albumin. For instance, the botulinum toxin and a stabilizing agent for botulinum toxin may be dissolved in a solvent and the solution may sterilely be filtered and filled into an ample, a vial, and the like to prepare the pharmaceutical composition of the present invention. Alternatively, the botulinum toxin may be dissolved in a solvent in which a stabilizing agent for botulinum toxin has previously been dissolved and the solution may sterilely be filtered and filled into an ample etc. A solvent may include distilled water for injection, physiological saline, 0.01M to 0.1M phosphate buffer, etc., which may optionally be mixed with ethanol, glycerol, etc.

Alternatively, the botulinum toxin and a stabilizing agent for botulinum toxin may be dissolved in a solvent, and the solution may sterilely be filtered and filled into a vial etc., followed by lyophilization to prepare the pharmaceutical composition of the present invention. Still alternatively, the botulinum toxin and a stabilizing agent for botulinum toxin may be mixed together and the mixture may then be sterilely filled into a vial etc. to prepare the pharmaceutical composition of the present invention.

Specifically, to the purified botulinum toxin may be added a stabilizing agent for botulinum toxin, preferably a human serum albumin, more preferably a human serum albumin for therapy proved for safety in human, at a final concentration of 0.1 to 5 mg/mL, preferably 0.5 to 2 mg/mL, and the mixture may be stored with cooling, freezing or by lyophilization.

The therapeutic medicament of the present invention, as occasion demands, may further be supplemented with additives such as sugars e.g. mannitol, glucose or lactose, a saline, sodium phosphate, and the like. The pharmaceutical composition of the present invention may usually be at pH of 3 to 8, preferably 4 to 7, more preferably 5 to 7.

The botulinum toxin contained in the therapeutic medicament of the present invention may be at such an amount as efficacious for use in the present invention. In case that a stabilizing agent for botulinum toxin is contained in the therapeutic medicament of the present invention, the agent may be at an amount sufficient for stabilizing the botulinum neurotoxin.

The therapeutic medicament of the present invention may most suitably be used as a therapeutic medicament for treating a patient suffering from a disease with muscle overactivity who has a neutralizing antibody to a type A1 botulinum toxin. The objective diseases for which the therapy for decreasing local, muscle overactivity is aimed herein includes strabismus, blepharospasm, hemifacial spasm, spasmodic torticollis, post-stroke spasticity, cerebral palsy, spasmodic dysphonia, headache such as migraine, chronic pain such as lumbago, the stiffness in the shoulders, paresis occurring at the onset of Parkinson disease or multiple sclerosis, myofascial pain syndrome, spasm of the masticatory muscles, chronic anal fissure, overactive bladder, bruxism, facial myokymia, tic, local dystonia, or wrinkle. The myofascial pain syndrome, a disease with tension bands of solid stiffness in the muscles produced due to acute muscular damage or repetitive overload (overuse) of the muscles and with a strong pain, is known that muscular tension in hands and legs is exceedingly accelerated post-apoplectically or in association with the onset of cerebral palsy, Parkinson disease or multiple sclerosis. It is also known that headache such as chronic migraine occurs due to abnormal muscle overactivity in the neck and the shoulders and that muscular tension may abnormally be accelerated due to fatigue in the muscles or sustained bad carriage to thereby ultimately induce chronic pains such as lumbago, pains at the neck or the back or the stiffness in the shoulders.

A disease with a muscle overactivity to be treated with the therapeutic medicament of the present invention is preferably a disease where rapid relaxation of a muscle overactivity is needed, i.e. a disease that needs to be treated with a therapeutic medicament having immediate efficacy. Such a disease with a muscle overactivity includes one where a medicament is administered by adjusting a dose until an effective dose is determined and systemic one where the treatment is done with cumulative efficacy. A systemic disease with a muscle overactivity includes systemic dystonia, systemic contracture, post-stroke spasticity, cerebral palsy, Parkinson disease and multiple sclerosis.

The therapeutic medicament of the present invention may be administered at an effective amount. When administered to human, its preferable route of administration is topical administration, more preferably, intramuscular administration. Timing and a dose of administration are not particularly limited and may vary depending upon severity of symptoms etc. A dose may vary depending upon severity of symptoms, age, sex, weight, site and route of administration but, for instance, 0.01 to 2,000 units, preferably 0.5 to 600 units are once administered intramuscularly for adults. One unit is defined herein as an amount of the toxin with which a half of mice die when administered intraperitoneally (1 $LD_{50}$). A total dose for patients is within a range of about 0.01 to 2,000 units.

After injection, therapy proceeds while it is confirmed in all patients that there is no extensive decrease in local tension in the muscles other than those of interest observed with no systemic or local adverse effects and that functional alleviation in the muscles to be treated is seen using an electromyograph.

The present invention also provides a pharmaceutical preparation comprising as an active ingredient the highly purified type A botulinum toxin from HA-negative type A *Clostridium botulinum* isolated as infant botulism pathogen and a method for the treatment by using said pharmaceutical preparation as a therapeutic medicament for decreasing local, muscle overactivity in a disease with a muscle overactivity. The highly purified botulinum toxin, a disease with a muscle overactivity, a route of administration and a process for preparing the same are described hereinabove.

EXAMPLE

The present invention is explained in more detail by means of the following Examples but is not construed to be limited thereto.

Example 1

Purification of NTX from Type A2 *Clostridium botulinum*

Using Chiba-H strain, type A *Clostridium botulinum* isolated from patients suffering from a disease with a muscle overactivity, botulinum type A, M toxin, was purified as described by Sakaguchi G., Biochemical aspects of botulism: Purification and oral toxicities of *Clostridium botulinum* progenitor toxins, 21-34, Lewis G E., 1981, Academic Press, New York.

The botulinum M toxin was dialyzed against 10 mM phosphate buffer (pH 7.5), adsorbed to DEAE Sepharose column equilibrated with the same buffer, and eluted with 0 to 0.3 mol/L NaCl gradient of the same buffer to separate the neurotoxin (NTX) from non-toxin proteins (NTNH). The obtained highly purified NTX (A2 NTX) was concentrated with YM-10 membrane (Amicon) to 1 mg/mL, dialyzed against 50 mM phosphate buffer (pH 7.5) and stored at −80° C. till use, which was used as A2 NTX.

Example 2

Purification of LL Toxin and NTX from Type A1 *Clostridium botulinum*

Using 62A strain, HA-negative type A1 *Clostridium botulinum*, the culture and purification of toxins were performed as described by Sakaguchi G. as in Example 1 to give LL toxin and M toxin. Furthermore, NTX was purified from M toxin and used as A1 NTX.

Example 3

Construction of Model Rat with Decreased Response to Botulinum Toxin

LL toxin from 62A strain was diluted with 0.1 mol/L phosphate buffer (pH 6.4) to 0.3 mg/mL and put in a dialysis apparatus. Dialysis was performed at 30° C. for 7 days with a buffer for conversion into toxoid in an amount 100-fold higher than that of the diluted toxin. After dialysis, the toxoid was stored at 4° C. and proved to be nontoxic by administration to mice.

The toxoid at 10 μg/head was subcutaneously administered to rats (S/D, 6 weeks old, female) for three times at an interval of 2 weeks. The rats were bled 6 and 10 weeks after the 1st administration. Elevation in a neutralizing antibody titer due to A1 NTX was confirmed. A1 NTX, the same kind as the toxoid, at $2 \times 10^6$ U/head was administered to the gastrocnemius muscle of the left hind leg to confirm that CMAP amplitude was not decreased and the symptoms were not altered a day after the administration. CMAP measurement was done as described in WO2007/125604. A neutralizing antibody titer in rat sera 10 weeks after the immunization is shown in Table 1.

TABLE 1

| Rat Nos. | Neutralizing antibody titer (IU/mL) |
|---|---|
| 1 | 11.1 |
| 2 | 9.9 |
| 3 | 5.5 |
| 4 | 14.5 |
| 5 | 1.7 |
| 6 | 20.5 |
| 7 | 17.6 |
| 8 | 2.8 |
| 9 | 17.7 |
| 10 | 10.9 |
| 11 | 1.6 |
| 12 | 4.6 |
| 13 | 10.7 |
| 14 | 6.8 |
| 15 | 5.6 |
| 16 | 5.4 |
| 17 | 2.8 |
| 18 | 55.7 |
| 19 | 12.5 |
| 20 | 0.8 |
| 21 | 10.2 |
| 22 | 4.4 |
| 23 | 4.3 |
| 24 | 8.9 |
| 25 | 3.7 |
| 26 | 6.3 |
| 27 | 6.4 |
| 28 | 4.8 |
| 29 | 3.2 |
| 30 | 2.3 |

Example 4

Administration of NTX to Model Rat with Decreased Response to Botulinum Toxin As shown in Table 2, model rats with decreased response to botulinum toxin were divided into two groups so that the rats in each group may have approximately the same mean neutralizing antibody titer when administered with LL toxin toxoid from 62A strain. To each group was administered A1 NTX or A2 NTX at $2 \times 10^6$ U/head at the gastrocnemius muscle of the left hind leg and CMAP amplitude was measured a day after the administration.

TABLE 2

| Toxin administered | Rat Nos. | Neutralizing antibody titer (IU/mL) |
|---|---|---|
| A2 NTX | 1 | 11.1 |
|  | 3 | 5.5 |
|  | 5 | 1.7 |
|  | 10 | 10.9 |
|  | 12 | 4.6 |
|  | 15 | 5.6 |
|  | 16 | 5.4 |
|  | 17 | 2.8 |
|  | 19 | 12.5 |
|  | 20 | 0.8 |
|  | 21 | 10.2 |
| A1 NTX | 2 | 9.9 |
|  | 4 | 14.5 |
|  | 6 | 20.5 |
|  | 7 | 17.6 |
|  | 8 | 2.8 |
|  | 9 | 17.7 |
|  | 11 | 1.6 |
|  | 13 | 10.7 |
|  | 14 | 6.8 |
|  | 18 | 55.7 |
|  | 22 | 4.4 |

As a result, it was shown that no change in CMAP amplitude was observed in A1 NTX group due to neutralization by antibodies present within the body of rats whereas, in A2 NTX group, CMAP amplitude was decreased to indicate a neuromuscular transmission blocking effect (FIG. 2).

Example 5

Reaction of Human Serum Containing Anti-Type A1 Botulinum Toxin Antibody with NTX Six humans inoculated with botulinum toxoid for laboratory use were bled and an antibody titer to type A1 botulinum toxin in sera was measured. A type A toxoid contained in the toxoid as used is one from 97A strain, and like 62A strain, is classified into type A1. These sera were diluted to 10 mIU/mL, which is a supposed antibody titer in sera from a patient with decreased response to botulinum toxin. Each of test toxins, A1 NTX and A2 NTX, were diluted to 10 U/mL. Each of the diluted sera and each of the test toxins were mixed in equal amounts for reaction at room temperature for 1 hour. The reaction mixture at 0.1 mL was administered to rats at the gastrocnemius muscle of the left hind leg and CMAP amplitude was measured a day after the administration. As a control, each of the toxins was administered to rats at 0.5 U/head and the same measurement was performed.

Figure 3:
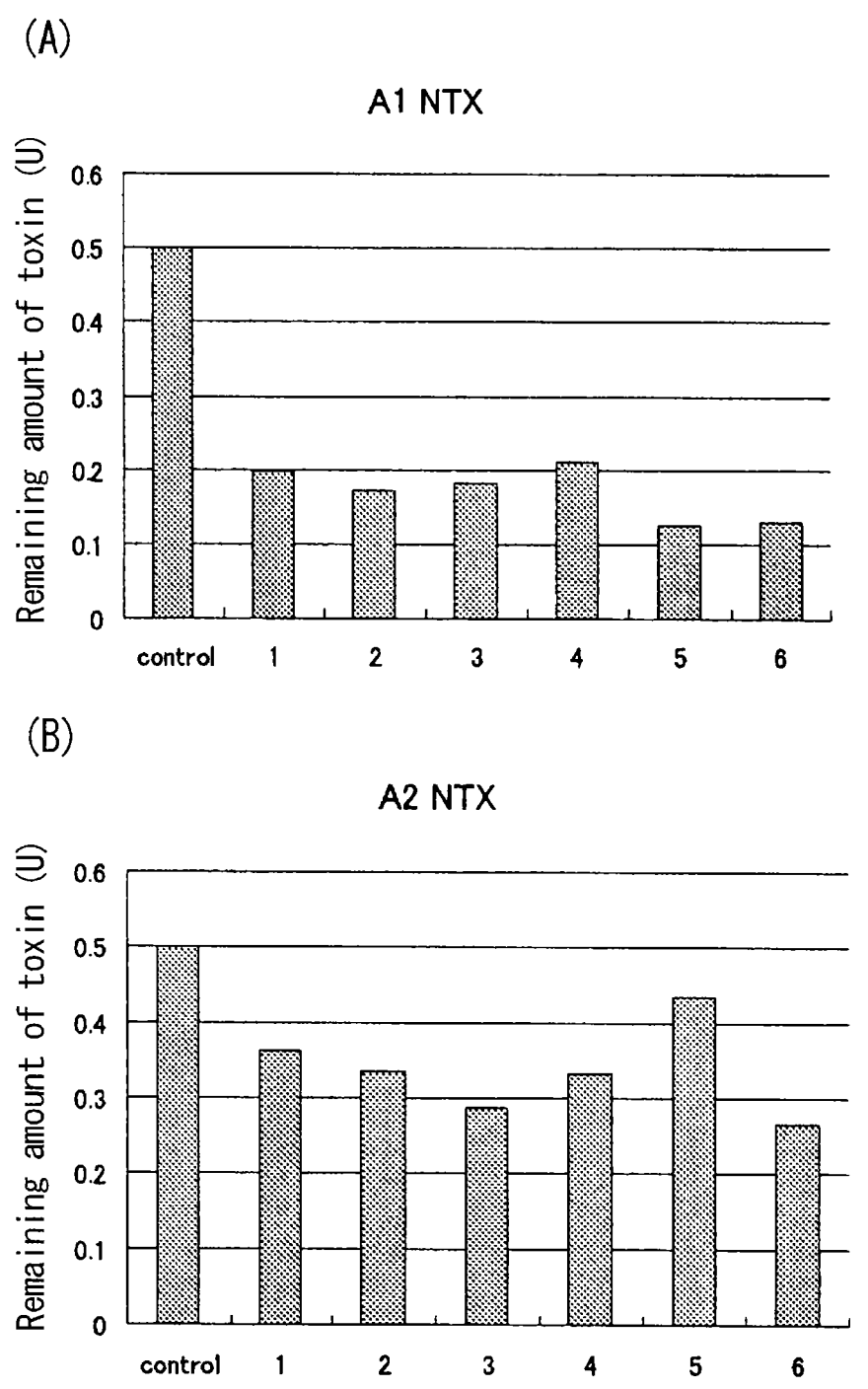

As a result, as shown in FIG. 3, in the groups where A1 NTX is used as a test toxin (FIG. 3A), a remaining amount of toxin was 0.13 to 0.21 U, indicating that 60% or more of the toxin was neutralized. On the other hand, in the groups where A2 NTX is used as a test toxin (FIG. 3B), a remaining amount of toxin was 0.26 to 0.43 U, indicating that more than a half of the toxin remained. The groups with A1 NTX and the groups with A2 NTX were subject to Tukey Multiple Comparison to prove significance in difference between the A1 NTX and A2 NTX groups.

INDUSTRIAL APPLICABILITY

The highly purified botulinum toxin (A2 NTX) according to the present invention from HA-negative *Clostridium botulinum* isolated from infant botulism pathogen, as not comprising HA, is less likely to induce antibody production and is less likely to attenuate in its efficacy after repetitive administration. Furthermore, A2 NTX does not cause a problem of decrease in clinical response caused by a neutralizing antibody to a type A1 botulinum toxin produced when a patient is treated with a pharmaceutical preparation comprising a type A1 botulinum toxin. Therefore, A2 NTX is particularly useful for use as a medicament for treating various diseases with muscle overactivity.

The invention claimed is:

1. A method for treating a patient who has a neutralizing antibody to a type A1 botulinum toxin, said method comprising administering A2 NTX to the patient.

2. A method for treating a patient suffering from a disease with muscle overactivity who has a neutralizing antibody to a type A1 botulinum toxin, said method comprising administering A2 NTX to the patient.

3. The method of claim 1, wherein the administering is topical.

4. The method of claim 1, wherein the administering is intramuscular.

5. The method of claim 4, wherein a dose administered is 0.01 to 2000 units, wherein one unit is a mouse $LD_{50}$ amount of A2 NTX.

6. The method of claim 4, wherein a dose administered is 0.5 to 600 units, wherein one unit is a mouse $LD_{50}$ amount of A2 NTX.

7. The method of claim 2, wherein the disease with muscle overactivity is selected from the group consisting of strabismus, blepharospasm, hemifacial spasm, spasmodic torticollis, post-stroke spasticity, cerebral palsy, spasmodic dysphonia, migraine headache, lumbago, shoulder stiffness, paresis occurring at onset of Parkinson's disease, paresis occurring at onset of multiple sclerosis, myofascial pain syndrome, spasm of a masticatory muscle, chronic anal fissure, overactive bladder, bruxism, facial myokymia, tic, local dystonia, and wrinkle.

8. The method of claim 1, wherein the A2 NTX is administered as a mixture comprising the A2 NTX and a stabilizing agent.

9. The method of claim 8, wherein the stabilizing agent is a human serum albumin.

10. The method of claim 8, wherein the mixture comprises a final concentration of 0.1 to 5 mg/ml of the stabilizing agent.

11. The method of claim 8, wherein the mixture comprises a final concentration of 0.5 to 2 mg/ml of the stabilizing agent.

12. The method of claim 9, wherein the mixture comprises a final concentration of 0.1 to 5 mg/ml of the stabilizing agent.

13. The method of claim 9, wherein the mixture comprises a final concentration of 0.5 to 2 mg/ml of the stabilizing agent.

14. The method of claim 8, wherein the mixture further comprises a solvent selected from the group consisting of distilled water, physiological saline, and 0.01 M to 0.1M of a phosphate buffer.

15. The method of claim 9, wherein the mixture further comprises a solvent selected from the group consisting of distilled water, physiological saline, and 0.01 M to 0.1M of a phosphate buffer.

16. The method of claim 14, wherein the mixture further comprises ethanol or glycerol.

17. The method of claim 15, wherein the mixture further comprises ethanol or glycerol.

18. The method of claim 8, wherein the mixture has a pH of 3 to 8.

19. The method of claim 8, wherein the mixture has a pH of 4 to 7.

20. The method of claim 8, wherein the mixture has a pH of 5 to 7.

* * * * *